United States Patent [19]

Kagitani et al.

[11] Patent Number: 4,587,122

[45] Date of Patent: May 6, 1986

[54] FIBRONECTIN-DEXTRAN-DRUG COMPLEX AND METHOD OF PREPARATION THEREOF

[75] Inventors: Yoshio Kagitani, Kashihara; Yasuo Ueda, Hirakata; Kozi Munechika, Yawata; Satoshi Morimoto, Nagaokakyo; Shirou Komeda, Tondabayashi; Kenji Tanaka, Yamatokoriyama; Kazumasa Yokoyama, Toyonaka, all of Japan

[73] Assignee: The Green Cross Corporation, Osaka, Japan

[21] Appl. No.: 726,321

[22] Filed: Apr. 23, 1985

[51] Int. Cl.⁴ .................... C07G 7/00; A61K 35/16; A61K 37/04; A61K 31/72
[52] U.S. Cl. .................... 424/101; 530/392; 530/410; 530/813; 514/21; 514/8
[58] Field of Search .................... 260/112 B; 424/101; 514/21, 8

[56] References Cited

U.S. PATENT DOCUMENTS

| | | | |
|---|---|---|---|
| 4,210,580 | 7/1980 | Amrani | 260/112 B |
| 4,315,906 | 2/1982 | Gelder | 260/112 BX |
| 4,341,764 | 7/1982 | Wallace et al. | 260/112 BX |
| 4,376,765 | 3/1983 | Trovet et al. | 424/177 |
| 4,391,749 | 7/1983 | Engvall et al. | 260/112 BX |

FOREIGN PATENT DOCUMENTS 114685  8/1984  European Pat. Off. .

*Primary Examiner*—Howard E. Schain
*Attorney, Agent, or Firm*—Cushman, Darby & Cushman

[57] ABSTRACT

The drug such as antitumor agents or antibiotics can preferentially be carried to a morbid part, for example, injured tissue and tumor site by administering its complex with fibronectin combined through an oxidized dextran to repair the morbid part. The complex is prepared by reacting the drug, an oxidized dextran having a cleaved structure of aldohexopyranose ring, and fibronectin.

14 Claims, No Drawings

FIBRONECTIN-DEXTRAN-DRUG COMPLEX AND METHOD OF PREPARATION THEREOF

This invention relates to a novel fibronectin-drug complex and the preparation thereof. More particularly it relates to a method of preparing a fibronectin-dextran-drug complex resulting from combining a fibronectin, which has a high affinity for a morbid part such as an injured tissue or a tumor site with a drug capable of protecting and repairing these tissues and sites and thus the prepared complex.

It is a common practice to administer various drugs systemically to prevent the suppuration of a wounded site, to promote the repair of an inflamed site, and to destroy cancer cells. In this case it is unavoidable at present to administer a large amount of the drug in order to attain to a sufficient concentration to exert its effect.

Especially in the case of administering an antitumor substance, since the dose giving a manifest effect and that giving a manifest side effect are frequently in close proximity, the large-amount administration is often compelled to be discontinued owing to the manifestation of the side effect even when a promising effect can be expected, leading thus to a fatal result. In order to avoid such situations, it is necessary to accumulate the drug specifically in the morbid part as an injured tissue such as a wounded site and an inflamed site, or a cancer site.

The inventors have made intensive studies based on the idea that, in order to accumulate the drug specifically in the local region, the drug should be transported in a high concentration to the local region by using as a carrier a substance which has a high affinity for the morbid part such as a wounded site, an inflamed site, and a cancer cell proliferation site.

An example of such a carrier is already known in the use of, for example, a cancer-specific antibody as the carrier of an antitumor substance. In this case, the specific accumulation does not take place unless the target cancer has an antigen which is specific to the antibody used as the carrier. Thus, this method has the disadvantage in that its effectiveness is exhibited only in very limited cases. Further, many of the antibody carriers being a foreign protein for human being, its administration would involve a serious antigen problem.

There is no clear example of a carrier being used for an antibiotic. However, a straightforward example of a serious side effect caused by a large-amount administration required for acquiring an effective concentration is seen in the administration of chloramphenicol. Even in this case, it would be possible to avoid the side effect if the main effect can be manifested at a small dose. The same applies to an anti-inflammatory agent as to the anti-biotic. Especially for these agents and substances, there exists no specificity like an antigen-antibody reaction in the morbid part, and hence no carrier has been found and no specific accumulation has been tried in the prior art.

The inventors have found that a fibronectin administered artificially accumulates specifically in morbid parts such as a wounded site, an inflamed site, and if the fibronectin is used as a carrier the drug will be accumulated in the target morbid part irrespective of the presence or absence of a specificity like a foreign antibody on the concerned part of the living body, improving the chemotherapeutic index of an individual drug. Accordingly, they have prepared various fibronectin-drug complex (Hereinafter referred to simply as complex) by combining various drugs used in the treatment of various diseases with a fibronectin, confirmed their affinity for the morbid part, and thus accomplished this invention.

In preparing the complex, it has been found that an oxidized dextran which has a group capable of combining with both of the drugs and fibronectin is used to obtain a complex of fibronectin and the drugs which combine through dextran residue.

Thus, this invention relates to a fibronectin-dextran-drug complex in which fibronectin is connected through a dextran residue with the drug which is selected from the group consisting of an antitumor agent, an antibiotic and an antiinflammatory agent, the dextran residue being resulted from the partial oxidation of dextran.

Various names have been given to the fibronectin by the investigators concerned. As can be seen in Shuichi Tsukasaki: Tanpakushitsu, Kakusan, Koso (Protein, nucleic acid, and enzyme); Vol. 25, No. 10, 890-905 (1980), it is also designated as cold insoluble globulin, LETS protein, opsonic protein, and cell surface protein. Any of the fibronectins designated as above may be used in this invention. The fibronectin is present, for example, on the cell surface, in the extracellular substrate and in the plasma, and generally is collected and purified from these. Its principal component is dimers, but it contains also monomers. Some of its properties are shown below.

Mobility of main fraction: $\alpha$2-globulin; molecular weight of main fraction: $4.3-4.5 \times 10^5$; isoelectric point: 5.3-6.0; sugar content: about 5%; characteristic as substrate protein: A cross linkage is formed between fibronectins or between a fibronectin and a fibrin-$\alpha$-chain by factor XIII.

The fibronectin used in this invention may contain a small amount of low molecular weight fractions.

The drugs which can be used in this invention means those which have a promising antitumoral, antibacterial or antiinflammatory property and which can be combined with a fibronectin through an oxidized dextran. Although daunomycin, adriamycin, mitomycin, cephalothin, penicillin G, and secretin will be exemplified, among which daunomycin, and adriamycin are preferable for controlling cancer cells, this invention is not to be limited to these.

The oxidized dextran used in this invention is not specifically limited, and is preferably selected from ones having a molecular weight of 1,000 to 2,000,000. It is prepared by partially oxidizing a dextran according to a conventional method, for example, by use of alkali metal periodide, so that the ring-cleavage of the aldohexopyranose ring of dextran is effected in dextran molecule, as shown by the following formula.

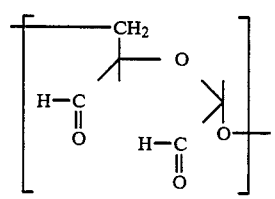

The ring-cleavage is preferably effected in 10-100% in the molecule of dextran.

The oxydation is carried out, for example, by adding 100 to 1400 mg of sodium periodide to a solution containing 500 mg of dextran, and allowing reaction at 10° C.-50° C. for 2 to 24 hours. The reaction mixture is concentrated and purified by, for example, dialysing against distilled water followed by drying preferably by lyophilization.

In the preparation of the present complex, three methods can be used namely a method to mix and react fibronectin, the oxidized dextran and the drug simultaneously, one to react the fibronectin with the oxidized dextran followed by reaction with the drug and one to react the drug with the oxidized dextran followed by reaction with the fibronectin, among which methods the third one is preferable.

The reaction is conducted in an aqueous solution of pH 5 to 9, preferably 6-8, and preferably in a buffer solution. Preferred reaction temperatures are 10° to 40° C., particularly room temperatures or lower. The reaction periods are generally 1 to 24 hours, and preferably 3 to 15 hours. In any of the above reactions, the molar ratio of the drug per the oxidized dextran combined is in a range of 2 to 200:1. Needless to say, the physiologically active substance is preferably added in excess of the fibronectin.

Thus, in the reaction between the drug and the oxidized dextran, it is preferred to combine 2-200 moles of the drug per 1 mole of the oxidized dextran. For this purpose, the reaction is preferably conducted by adding the oxidized dextran in a final concentration of 0.05-10 W/V % and the drug in a final concentration of 1-10 W/V % to an aqueous medium (preferably a phosphate buffer solution) of pH 5-9, preferably 6-8, and stirring the solution for about 1-about 15 hours. Thus the dextran-drug complex is obtained. The unreacted drug can be removed from the reaction mixture by means of a chromatography using a molecular sieve such as Toyopearl HW40 (made by Toyo Soda Inc.) or other methods known per se.

The reaction between the dextran-drug complex and fibronectin is conducted, in a large excess of the former by adding fibronectin in a final concentration of 0.1-3 W/V % to an aqueous solution containing the dextran-drug complex in a final concentration, for example, of 1-30 W/V %, and stirring the mixture for about 1 to about 40 hours.

The thus obtained objective complex of the present invention can be purified and collected by the procedures using, for example, gel filtration carrier, ion exchanger and gelatin-sepharose. The complex is made into a medical preparation such as frozen solution or lyophilized dryness after being sterile-filtered and placed in vials. The preparation contains the complex in which the molar ratio of the drug and fibronectin combined is 20-100 moles of the former per mole of the latter.

The complex of the present invention effectively accumulates at the morbid parts in the body so that its toxicity is extremely small to the normal parts. Especially, the complex of an antitumor drug such as daunomycin or adriamycin has a low chemotherapeutic index and is useful for controlling a cancer of mammals such as human, cattle, horse, mouse and dog. Also, the complex of the other drug is useful for the preferential accumulation at the morbid parts as is seen in European patent application Publication No. 114685 (applied partially common inventors of the present application and published on 1st, August, 1984) in which fibronectin-physiologically active substance such as mitamycin, cephalothin, penicillin G or secretin, which is linked by the aid of protein cross-linking agent such as glutaraldehyde is disclosed effective for this purpose.

The complex of the present invention may clinically administered to the patient, for example, in a physiological saline solution containing 10-300 mg of the complex in 0.05-5 ml, by intravenous injection or dropping in an appropriate dose depending upon the age of the patient and symptone and course of the disease, relying on the amount of the drug.

The present invention will be illustrated more concretely by way of Examples and Test Examples, which do not limit the invention.

In the Examples, the oxidized dextran used is an about 50%—oxidized dextran which was prepared by reacting 0.5 g of dextran having a molecular weight of 10,000 with 0.64 g of sodium periodate in distilled water, in a dark room for 3 hours, dialysing the reaction mixture against water to purify the yielding oxidized dextran, and lyophilizing the dialysate. Yield; 0.43 g.

Example 1

In 100 ml of a 50 mM phosphate-buffered physiological saline solution (pH 8.0) were dissolved 0.01 mM (10 mg) of the oxidized dextran, and 0.18 mM (10 mg) of adriamycin. The solution was allowed to stand at a room temperature for 2 hours to proceed with a reaction. Unreacted adriamycin was removed from the reaction mixture by gelfiltration using Sephadex ®-G25. To the solution was added 1 mg of glycin. The solution was lyophilized to obtain 18 mg of purified dry dextran-adriamycin complex. Ten mg of the thus obtained complex and 100 mg of fibronectin were reacted in 10 ml of a 10 mM phosphate-buffered physiological saline solution (pH 7.5) for 3 hours while ultrasonically stirring.

The reaction mixture was applied to a gelatin-Sepharose column (d=2.5 cm, 1=20 cm). After the column was well washed with the same buffered saline solution, a fraction absorbed by the gelatin-Sepharose was eluted with 8M urea solution and dialysed against the said buffered physiologically saline solution (pH 7.5) to obtain 60 mg of the objective adriamycin-dextran-fibronectin complex in which the molar ratio of the effective components contained is adriamycin:fibronectin=54:1 (determined by absorbance at 280 nm and 495 nm).

EXAMPLE 2

To 100 ml of a 50 mM phosphate-buffered physiological saline solution (pH 8.0) were dissolved 0.01 mM (10 mg) of the oxidized dextran and 0.19 mM (10 mg) of daunomycin, resulting solution was allowed to stand for 2 hours at a room temperature.

To the reaction mixture was added 10 ml of a 50 mM phosphate-buffered physiological saline solution (pH 7.5) containing 200 mg of fibronectin in 10 ml, and stirred ultrasonically for 3 hours to complete a reaction. The reaction mixture was subjected to gel-filtration using Sephadex ®-G25 to remove a lower molecular weight fraction, and then subjected to gelatin-Sepharose column chromatography as in the preceeding Example 1 to obtain a 8M urea solution containing the objective complex. The solution was well dialysed against a 10 mM phosphate-buffered physiological saline solution (pH 7.5) to obtain 145 mg of the objective daunomycin-dextran-fibronectin complex in which the molar ratio of the effective components contained is daunomycin:fibronectin=80:1.

Test Example 1

The adriamycin-fibronectin complex and the daunomycin-fibronectin complex obtained in Examples 1 and 2, respectively, were each tested for antitumor activity by the following method.

Test animals bearing cancer cells were prepared by transplanting subcutaneously $10^6$ Yoshida sarcoma cells to Donryu-strain rats (10 rats a group). Four days after the transplantation, the complex of the invention was administered intraveneously to the test animals via tail vein once a day in a dose of 1 mg/kg in terms of the drug for consecutive 4 days. Eleven days after the transplantation, the animals were sacrificed, and the tumors separated were weighed.

The results are shown in Table 1 together with those of the drugs only.

TABLE 1

| Drug | Dose (mg/kg/day) | Weight of tumor (g) |
| --- | --- | --- |
| No treatment | — | 4.83 ± 1.57 |
| Fibronectin | — | 4.91 ± 1.18 |
| Adriamycin | 1.0 | 1.45 ± 0.41 |
| Adriamycine-dextran-fibronectin complex | 1.0 (in terms of adriamycin) | 0.63 ± 0.32 |
| Daunomycin | 1.0 | 1.74 ± 1.05 |
| Daunomycin-dextran-fibronectin complex | 1.0 (in terms of daunomycin) | 0.88 ± 0.38 |

What is claimed is:

1. A method of preparing a fibronectin-dextran-drug complex in which fibronectin is connected through an dextran with a drug, which comprises reacting fibronectin, an oxidized dextran having aldohexopyranose ring-cleaved structure of the formula

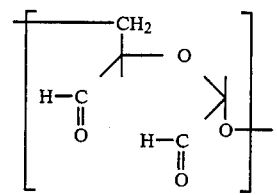

and a drug which is selected from the group consisting of an antitumor agent, an antibiotic and an antiinflammatory agent, and has a group capable of combining with the oxidized dextran.

2. A method of claim 1, wherein the reaction is carried out by reacting the drug with the oxidized dextran to form a drug-dextran complex, and then reacting the resulting complex with fibronectin.

3. A method of claim 1, wherein the drug is an antitumor agent selected from the group consisting of adriamycin and daunomycin.

4. A method of claim 2, wherein the reaction is carried out in a ratio of 1-10 parts by weight of the drug, 0.05-10 parts by weight of the oxidized dextran; and 1-30 parts by weight of the resulting complex and 0.1-3 parts by weight of fibronectin.

5. The method of claim 2, wherein the reaction is carried out in a room temperature or lower.

6. The method of claim 1, wherein the drug is selected from the group consisting of mitomycin, cephalothin, penicillin G and secretin.

7. The method of claim 1, wherein the oxidized dextran has a molecular weight of 1,000-2,000,000.

8. The method of claim 1, wherein the oxydized dextran has 10-100% of the cleaved aldohexopyranose structure.

9. A fibronectin-dextran-drug complex obtained by a method according to claim 1.

10. A fibronectin-dextran-drug complex obtained according to a method of claim 2.

11. A fibronectin-dextran-drug complex of claim 10, wherein the molar ratio of fibronectin:drug is 1:20-100.

12. A fibronectin-dextran-drug complex of claim 10, wherein the molar ratio of dextran:drug is 1:2-200.

13. A method for target-protecting or repairing a morbid part of cancer site, wounded site or inflamed site in the body of a mammal, which comprises administering a fibronectin-dextran-drug complex of claim 10 to said mammal in an effective amount in terms of the drug.

14. A method according to claim 12, wherein said complex has a molar ratio of fibronectin:drug of 1:20-100.

* * * * *